(12) United States Patent  
Raylman et al.

(10) Patent No.: US 6,236,880 B1
(45) Date of Patent: May 22, 2001

(54) RADIATION-SENSITIVE SURGICAL PROBE WITH INTERCHANGEABLE TIPS

(76) Inventors: Raymond R. Raylman, 1227 Van Voorhis Rd., Apt. 1, Morgantown, WV (US) 26505; Richard L. Wahl, 3572 Delhi Overlook, Ann Arbor, MI (US) 48103

( * ) Notice: Subject to any disclaimer, the term of this patent is extended or adjusted under 35 U.S.C. 154(b) by 0 days.

(21) Appl. No.: 09/316,402

(22) Filed: May 21, 1999

(51) Int. Cl.$^7$ .................................................. A61B 6/000
(52) U.S. Cl. ................................................................ 600/436
(58) Field of Search .................................... 600/310, 316, 600/407, 409–411, 433–436, 475; 250/337, 368, 370.06, 484.5, 458.1; 324/537, 628, 639, 754

(56) References Cited

U.S. PATENT DOCUMENTS

| | | | |
|---|---|---|---|
| 3,999,071 | 12/1976 | Siffert et al. | 250/370 |
| 4,999,504 | * 3/1991 | Braunlich et al. | 250/484.5 |
| 5,008,546 | 4/1991 | Mazziotta et al. | 250/366 |
| 5,036,201 | 7/1991 | Carroll et al. | 250/363.1 |
| 5,151,598 | 9/1992 | Denen | 250/336.1 |
| 5,170,055 | 12/1992 | Carroll et al. | 250/336.1 |
| 5,246,005 | 9/1993 | Carroll et al. | 128/654 |
| 5,325,855 | 7/1994 | Daghighian et al. | 128/653.1 |
| 5,441,050 | 8/1995 | Thurston et al. | 128/659 |
| 5,744,805 | 4/1998 | Raylman et al. | 250/370.01 |
| 5,932,879 | 8/1999 | Raylman et al. | 250/370.06 |
| 5,961,457 | 10/1999 | Raylman et al. | 600/436 |

* cited by examiner

*Primary Examiner*—George Manuel
(74) *Attorney, Agent, or Firm*—Flehr Hohbach Test Albritton & Herbert LLP

(57) ABSTRACT

A modular radiation detecting probe system includes a probe body having a handle portion and a distal portion to which an extension member is attached. The free end of the extension member is adapted to matingly attach and detach, one at a time, with various probe tips. An electronic signal acquisition system is disposed within the probe body and is coupled to receive a signal output from an attached probe tip. The acquisition system signal process the signal to discriminate between noise and a radiation signal detected by the probe tip. The probe body may include visual and/or audible devices to signal when the probe tip is adjacent a radiated area. The probe body may include a transmitted to transmit acquired signal data to an external signal processing unit, which may be a computer. Preferably the free end of the extension member includes a mechanism enabling identification of an attached probe tip such that the acquisition system may be normalized to compensate for different probe tip signal characteristics.

21 Claims, 3 Drawing Sheets

RADIATION-SENSITIVE SURGICAL PROBE WITH INTERCHANGEABLE TIPS

FIELD OF THE INVENTION

The invention relates generally to handheld probes used during surgical procedures, and more particularly to handheld probes used to detect radiation emissions from radionuclides.

BACKGROUND OF THE INVENTION

It is known in the art to examine the first (or sentinel) lymph node in the lymphatic system draining an area in which a cancerous growth is present. In the past, it was common to inject a non-radioactive dye into the tissue surrounding the primary tumor and then attempt to visually identify collection of the dye in the draining lymph nodes. The first lymph node visualized would be considered the sentinel lymph node. However this procedure is often non-optimal and is difficult to execute correctly. Extensive training is required and the technique has considerable difficulty with deeply located nodes, which may not be visible to the naked eye due to overlying tissue.

More recently, radionuclides have found use in guiding biopsy and surgical procedures. Radionuclides advantageously permit effective detection and treatment of disease, while minimizing harmful effects to the patient. For example, detection and treatment of malignant melanoma often involves surgical removal of the primary tumor and much of the lymphatic system draining the cutaneous tumor site. This procedure is performed to reduce the likelihood of further spread of the disease to distant areas and to identify lymph node metastases, so as to plan subsequent therapy. A similar approach has been followed in the management of breast cancer.

Radionuclides offer promise both in non-surgical survey procedures as well as in intraoperative procedures. For example, consider the task of identifying and removing only the sentinel lymph node(s) in the lymphatic system draining an area affected by tumor. A radiolabeled colloid tracer is injected subcutaneously or intradermally near the site of the primary tumor. The radioactive colloid tracer drains into the lymphatic system and becomes trapped in the first lymph node(s) in the chain of nodes. This first or sentinel node often is the first site to accumulate metastatic cancer cells. In some cases, more than one sentinel lymph node is identified.

Prior to surgery, the suspected region containing the sentinel lymph nodes is surveyed with a radiation detection probe. An appropriate probe helps localize the area of greatest radiation detection signal, which thus localizes the sentinel node position. This position is marked on the patient's skin to guide the surgeon in removing the node, or at the time of surgery, the node is identified through the skin or through a surgical incision. Alternately, the suspect area can be scanned with a gamma camera to permit identifying and marking the area of focal tracer uptake. A commonly used radiolabel is the gamma-emitter $^{99m}$Tc which is typically attached to sulfur colloid.

An intraoperative radiation sensitive probe, which may be the same probe used in the initial non-surgical survey, is then used to verify node identification and especially to locate the sentinel node during surgery.

Radionuclide-guided surgery has application in fields other than sentinel node detection, for example, localizing tumors using radiolabeled antibodies or other radiopharmaceuticals such as labeled peptides, phospholipid ether analogs, and other tumor-avid tracers. Commonly used radionuclides for labelling these tracers include gamma-emitters and X-ray emitters such as $^{99m}$Tc, $^{201}$Tl, $^{111}$In, $^{123}$I, and $^{125}$I, and beta-emitters such as $^{131}$I and $^{18}$F.

Several radiation sensitive probes are available commercially. U.S. Pat. No. 5,441,050 to Thurston (1995), assigned to Neoprobe Corp., discloses a solid handle whose tip includes a solid-state (CdZnTe) detector that is connected by a cable to a remote unit containing an analyzer and power source. The analyzer provides visual and audible radiation count rate information. A similar probe is also produced by Radiation Monitoring Devices. Each of these probes includes a collimator, which reduces the effects of background and scattered gamma rays.

Care Wise Medical Products Corp. produces a so-called C-Trak probe that utilizes a scintillator coupled to a photomultiplier tube to measure gamma ray flux. Capintec Inc. produces the so-called Gammed II product, which offers two probes: a CsI scintillator coupled to a silicon photodiode, or a silicon photodiode-equipped probe to detect gamma ray flux. Again, all of the probes include collimation.

Different surgical tasks and challenges require detection of different types of radiation, and detection by different sized probes. For example, when detecting radiation over relatively large areas, large-tipped probes are preferred as they exhibit greater detection sensitivity than small-tipped probes. This means that the radiation-containing focus can be identified more rapidly by the surgeon. However, the detection resolution of such probes is poor, and for more precise target resolution it is preferable to use small-tipped probes.

Unfortunately in the prior art, these goals are achieved only by replacing one probe or type of probe with another. At best, in an attempt to somewhat tailor the probe to the task at hand, some prior art probe systems offer interchangeable detector tip collimators. Unfortunately, the type of radiation to be detected by the probe remains the same, but the collimation characteristics may be user-changed. Further, the size of the probe itself is not changed, merely the collimation characteristics. A single probe unit may cost over $20,000 and requires periodic maintenance. Understandably, providing and maintaining a plurality of probes having different characteristics and/or sizes is a costly undertaking, which cost may be reflected in a higher medical bill to the patient.

What is needed is a radionuclide detecting probe whose detection characteristics and/or detector size may be readily changed. Preferably such probe should be modular in that changing the probe tip permits changing the detection characteristics and/of the detector size. Such probe should provide the user with audible and/or visual indications of relative strength of detected radiation, and should also provide for electronic enhancement of detected signal/noise. Preferably such probe should provide a wireless operation capability, to give greater freedom of movement to the practitioner using the probe. Ideally, the probe should also specifically conform to the shape of the user's hand to minimize fatigue.

The present invention provides such a probe.

SUMMARY OF THE PRESENT INVENTION

In a first aspect, the present invention provides a modular radiation-detecting surgical probe. The probe is modular in that probe tips are readily connected and disconnected from the probe body within a few seconds. The ability to use a common probe body with any of a number of interchangeable probe tips enables the medical practitioner-user to instantly change tips during the course of a procedure, and to select a tip whose operating characteristics are best tailored to the task immediately at hand. In addition, there are considerable cost savings in purchasing and maintaining a single probe body and several tips, as opposed to purchasing and maintaining several conventional probe units.

The probe body preferably houses a power source, and a data acquisition system that includes a preamplification unit that receives and pre-amplifies electrical signals from an attached probe tip, a signal discriminator unit, and controls to enable signal/noise enhancement of detected radiation signals. The probe body also houses at least one output device to signal (audibly and/or visually) at least relative detected radiation signal strength to the probe user. The probe body can house a battery power supply and, if desired, a wireless transmitter that transmits probe data to a nearby receiver or other signal processing unit. Alternatively, an umbilical cord may be used to electrically couple the probe body to an external power source and analysis unit. An articulatable goose-neck like coupler is attached to and extends from the distal end of the probe body. Alternatively, the probe tip may be mounted to a minimally invasive surgical device such as a laparoscope, bronchoscope, or thoracoscope, and coupled with the probe body by means of an elongated cord, for use in minimally-invasive surgical procedures.

Any of a number of interchangeable probes mate with and attach mechanically to the distal end of the coupler. The mating end of each probe is similar in size, for purposes of mating with the coupler and thus with the probe body and attached power and analysis unit. However the overall size and the detection characteristics of the various probe tips can vary. Indeed, the ability to rapidly disconnect one probe tip and connect another is one benefit of the present invention. Preferably electronics within the probe body senses the nature of the tip in use for purposes of normalizing detected signals for subsequent signal processing. As noted, the signal processing may occur within the probe housing and/or externally to the probe housing.

Other features and advantages of the invention will appear from the following description in which the preferred embodiments have been set forth in detail, in conjunction with the accompanying drawings.

DETAILED DESCRIPTION OF THE PREFERRED EMBODIMENT

Before describing the present invention in detail, it is useful to discuss why it may be necessary for a surgeon or other practitioner-user to change probe tips during a procedure or between procedures. As noted, it is important that the radiation detection characteristics of the probe (as determined by the particular probe tip) be tailored to the task at hand. It will be appreciated that each radionuclide emits its own unique energy spectra of gamma rays, x-rays and/or beta particles. For example, $^{99m}Tc$ emits a gamma ray with an energy of about 143 kev and is often used for sentinel node searching. Detecting such emissions is more effectively implemented using an inorganic scintillator detector such as CsI or NaI(Tl), or with a solid state detector such as CdZnTe. If a low-energy gamma-emitter is used, for example $^{125}I$, a mercuric iodide detector $HgI_2$ may be preferable.

Some applications may benefit from a beta-emitter such as $^{131}I$, in which case a thin solid state silicon wafer detector is preferred, for example a surface barrier detector that preferentially detects the short range electrons emitted by this radionuclide. Compared to other detector materials (e.g., CdZnTe) such thin silicon detectors exhibit diminished detection sensitivity for gamma rays, which is advantageous as the intent is to preferentially detect the beta emissions as these provide more precise localization information.

Although it is important that the radiation detection characteristics of the probe be suitable for the task at hand, it is also important that the size of the probe tip also be tailored to the application. Physically larger detectors exhibit greater detection sensitivity and are preferred for area searches, such as sentinel node detection in the breast or groin area. But large detectors have poor resolving power and are unsuitable to locate small tumors or lymph nodes, especially if the injection site is nearby or if the lymph nodes are small and in close proximity to each other such as in the head and neck region. Small probe tips are preferred for such tasks requiring more precise target resolution. Further, small probe tips may be more suitable for intraoperative use in minimally invasive surgery, such as via laparoscopy, and may also allow for the attachment of biopsy or ablation devices which can then be guided to the tumor by the probe signal.

Figure 1:
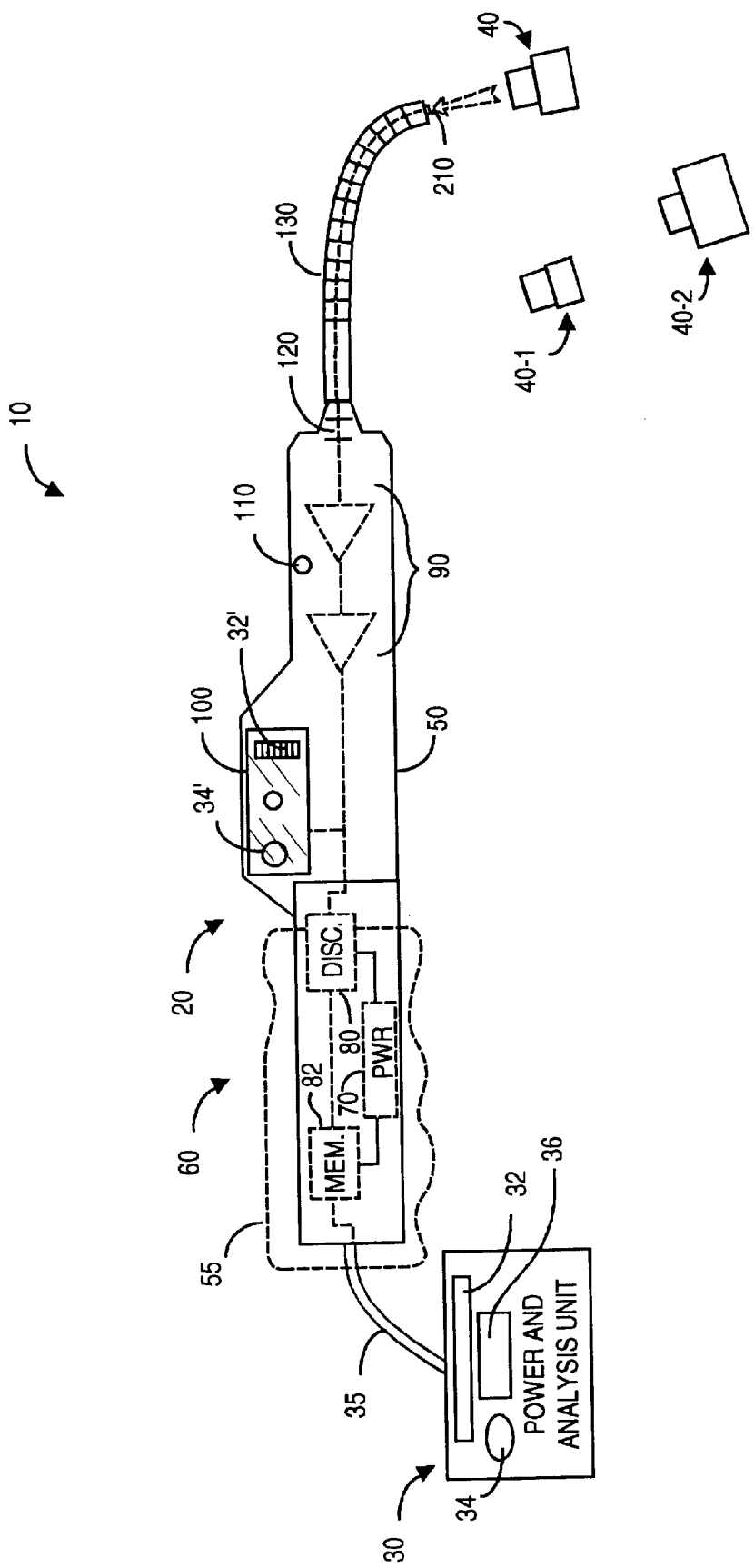
FIG. 1 is a schematic cross-section of a probe system, according to the present invention.

FIG. 1 depicts a probe system 10 according to the present invention that readily permits changing probe tips, to tailor the overall probe system to the immediate task at hand. System 10 includes probe 20, an external probe power and analysis unit 30, and at least one removable probe detector tip 40. FIG. 1 depicts several probe tips, e.g., 40, 40-1, 40-2 to denote that any of a variety of probe detector tips may be attached to the distal end of a probe, according to the present invention. The various tips may be sized differently and/or have different detection characteristics, although the probe-mating portion of each tip will be similar in size for attachment purposes. For solid state tips, sizes may vary from perhaps 5 mm (for a small tip), to 17 mm (for a medium tip) to perhaps 25 mm (for a large tip).

Unit 30 preferably provides bias voltage necessary to operate probe 20 and its associated electronics, assuming that probe 20 is not powered by a self-contained power source 70. Unit 30 may be battery operated, or may operate from 115/220 VAC and include an AC:DC circuit. Typically the voltages output from unit 30 will be in the range of 0 to ±10 VDC with an operating current of perhaps 0.5 mA to perhaps 3 mA. The bias voltage is routed via a cable 35 to the various electronics located within housing 60 of probe 20, as well as to the detector within the probe tip 40. Unit 30 may also include persistent and/or volatile storage unit 36, e.g., hard disk drive, magnetic tape drive, optical disk drive, solid-state memory, to maintain a record of the probe procedure. Unit 30 can also include an output module 32 and/or 34 to indicate relative detected signal information, Z-score data, among other useful information. Modules 32 and/or 34 may include visual and audible output devices.

In applications where probe 20 includes an internal power source 70, it will be appreciated that the remaining functions of unit 30 may be performed by a computer system, whether a desktop, laptop, palmtop or hand-held computing unit. Coupled to the output of probe 20 by a cable 35 (or wirelessly, e.g., by RF or IR), a computer 30 will execute software to carry out such analysis as is required and, optionally, to signal audibly and/or visually such data. If desired, memory within a computer unit 30 can store the data for subsequent analysis or re-analysis, permitting a replay of the data acquisition process. It will be appreciated that the ability of system 10 to interface with existing conventional computers further decreases the cost of owning and maintaining the overall system.

Probe 20 includes a probe central body portion 50 and a handle portion 60, within which are disposed a power unit 70 and a discriminator unit 80. Optionally, probe 20 may include memory 82 (e.g., compact flash) to store probe data obtained during a procedure. The stored probe data may then be downloaded (in realtime or after the fact) to a data processing system that may but need not be disposed within the probe body. The length of probe 20 (excluding the umbilical attachment 130 shown in FIG. 1) may be perhaps 18 cm, with a transverse dimension of perhaps 3 cm, although other sizes and shapes may instead be used.

Power unit 70 preferably comprises a pair of batteries configured to output perhaps ±6 VDC at a load current of a few mA, although other voltages may be used. If desired, unit 70 comprises a pair of batteries allowing probe 20 to function without requiring operating power from a source external to the probe body. Rechargeable batteries may be used, and may be coupled to external unit 30 for purposes of recharging.

It will be appreciated that the probe body serves both as a handle by which the surgeon or other practitioner user can manipulate the probe tip, and also as a housing for various electrical components associated with the probe system. Electrical preamplification and amplification stages 90 are disposed within the forward portion of body 50, closer to the probe detection tip. Disposing amplifier(s) 90 in the distal portion of the probe body serves to enhance signal/noise. The probe preferably is gas sterilizable and is relatively streamlined in its shape so as to provide minimum areas that might undesirably collect bodily fluids.

Body 50 preferably includes a display region 100 whereat data output can be displayed visually, for example on a light emitting diode ("LED") bargraph 32'. A bar-graph of LEDs could display, by changing bar-graph height, intensity of probe tip detected radiation signals and/or Z-score type data (described later herein). Alternatively, a single LED whose rate of blinking changes as a function of detected radiation signals could be used.

If desired, acoustic data output signals could also be provided, or could be provided instead of visual signals. For example, an audible tone that varies in frequency and/or strength with variations in detected radiation signals may be coupled to an acoustic transducer 34 and/or 34', as shown in FIG. 1. For example pulse-count signals from discriminator 80 may be coupled to a precision voltage waveform generator whose output drives a voltage controlled oscillator, whose oscillator output is coupled to transducer 34 and/or 24'. Conventional integrated circuits such as the InterCell ICL 8038 precision voltage-waveform generator may be used in such applications. If desired, any or all visual and/or audible output devices may be used to signal Z-score data (described later herein).

These various indicators can guide the practitioner in as the probe tip is moved adjacent to a source of radiation in the subject undergoing examination. In a typical application, the radiation source might be the sentinel node in a subject's lymphatic system, in which radiolabelled colloid or other tracer is now present.

Housing 50 preferably also includes a control 110 that permits discriminator 80 to selectively store background signals, e.g., signals not believed to be substantially radio-nuclide affected. As will be described later with respect to FIG. 3, storing a measure of background signals permits electronics associated with system 10 to subtract out a background signal component from radio-nuclide affected signals, to enhance effective signal-to-noise ("s/n").

As shown schematically in FIG. 1, electrical signals detected by probe 40 are carried by conductors 120, housed within a curved tube 130 to amplifier system 90, and the various other electrical components within probe 20. In a preferred embodiment, amplifier system 90 includes a high impedance preamplification unity gain stage (e.g., a Rel-Laps 724 preamplifier unit) and a pair of high gain amplifier units (e.g., Harris HA-2625) coupled to provide a gain of 27–30 db. In this embodiment, power unit 70 included two batteries coupled to output ±6 VDC. However implemented, the output from amplifier system 90 is coupled to the discriminator unit 80, whose pulse train output may be coupled to external unit 30, or signal processed and/or stored within probe 20.

Curved tube 130 may be a flexible or articulatable tube or a curved rigid tube, made perhaps of light weight plastic. However it is implemented, tube 130 permits the user to adjust the angle of the probe tip (and thus the detector) with respect to the probe body, thus promoting user comfort and minimizing fatigue associated with holding the probe. To further promote user comfort, the exterior surface of probe 20 may be covered with a removable covering whose shape has been custom molded to the hand of the individual user. This removable custom molded overpiece is shown in phantom in FIG. 1 as element 55.

The probe tip 40 may also be utilized in combination with minimally invasive surgical devices such as a laparoscope, bronchoscope, thoracoscope, and the like, for use with minimally invasive surgical techniques. In one embodiment, the probe tip 40 is mounted on the laparascope for internal use, and connected with an external probe body 20 via a cord or the like. The probe 20 may also be fully integrated with the laparascope or other minimally-invasive surgical device to provide simultaneous visual and radiation detection capabilities.

Preferably within unit 30, the incoming pulse train is subjected to pulse-height discrimination. Preferably the pulse height threshold values are user-selected, for example with a potentiometer or other control that may be attached to housing 50 of probe 20. Pulse-height discrimination signal processing can selectively filter out signals arising from scattered emissions and background sources of radiation, thus enhancing signal to noise ratio.

The height-discriminated pulses may be counted over a given time interval, and the resultant count rate information is displayed for the user. Further signal processing may be carried out by converting the digital pulse train to an analog signal, for example using a conventional frequency-to-voltage converter such as the Analog Devices AD650 unit. The resultant DC voltage permits an analog display of the radiation detection process, and also permits essentially real-time calculation of the Z-score statistical parameter. The display may be mounted on the probe itself (e.g., 32') and/or on unit 30 (e.g., display 32). Display 32' is especially advantageous in that the user need not look away from the region of interest to view the processed probe detection signals.

The Z-score is often used to determine whether the amount of signal from an area of interest differs from signals emanating from background regions. Z-score is defined by the following equation:

$$Z\text{-}score = \frac{s-n}{\sigma}$$

where s is the number of detected counts from an area of interest, n is the number of counts from a selected background region, and σ is the standard deviation associated with measurement of n. A larger Z-score implies that signals from the area of interest differ from background or noise signals.

Figure 2:
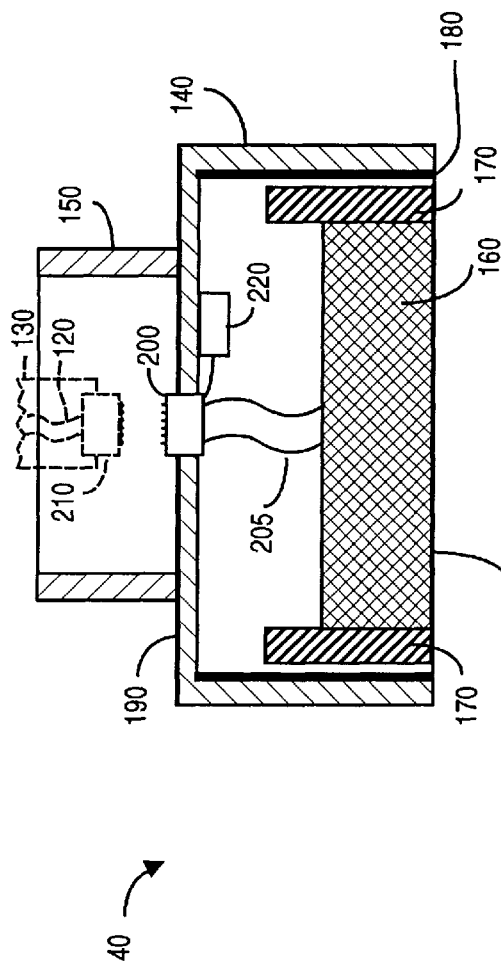
FIG. 2 is a simplified cross-section of a probe tip, according to the present invention.

FIG. 2 depicts a probe tip 40 intended for use with probe body 50, according to the present invention. Probe tip 40 includes an outer casing 140, typically a cylinder made of metal. Casing 150 includes a mating portion 150 that will interface with the distal tip of tube 130. Within casing 140 is a detector unit 160, typically retained by a cylindrical-like detector mount or holder 170 that is insertable into the enclosure defined within outer casing 140.

The inner wall surface of casing 140 is lined with a shield material 180 that shields against extraneous sources of background radiation activity. Without limitation, shield 180 may include materials such as lead, tungsten, gold, or depleted uranium. If desired, more extensive collimation can also be provided to limit the field-of-view of the detector. The front face (or patient-facing face) 185 of probe tip 40 preferably is covered by a thin foil that exhibits minimal radio-attenuation properties, HAVAR™, for example. The entire device may also be shielded by a plastic or HAVAR™ cover.

Detector unit 160 preferably is any of several types of detectors, including without limitation CdZnTe, CdTe, HgI2, silicon photodiode(s), silicon photodiode(s) with scintillator, surface barrier detector(s), avalanche photodiode(s), scintillator with photomultiplier tube(s), or ion-implanted-silicon detector(s). Such detector devices are commercially available, for example B101.1/P2 CdTe detectors sold by Radiation Monitoring Devices, Inc. Of course, custom fabricated detector devices may also be used.

The probe-facing end of probe tip 40 preferably is covered by a disk-shaped piece of metal 190. Preferably an electrical connector 200 is affixed to end 190 to provide connections, electrical and mechanical, between probe tip and probe 20. An exemplary hermetically sealed connector 200 is commercially available from Lemo, Inc. Wires 205 couple signals from detector 160 to connector 200.

When probe tip 40 is to be attached to probe 20, the distal portion of tube 130 is inserted into housing 150 such that detector connector 200 mates with a probe detector 210 located in the tube distal portion. The result is that mechanical and electrical connections are made between replaceable probe tip 40 and the remainder of system 10. In this fashion, signals from wires 205 are coupled via wires 120 to the various electronic components associated with system 10.

Probe tip 40 preferably includes an electrical and/or mechanical probe identification mechanism 220. Mechanism 220 enables probe system 10 to automatically identify the type of probe tip detector and/or probe size. The various electronics associated with system 10 can use this information to make appropriate electronic setting changes automatically.

Mechanism 220 can be passive and include, for example, a resistor network that will produce a given voltage when connected via connector 220, connector 210, and wires 120 to a reference voltage present in the electronics associated with system 10, electronics 80 and/or 90 for example. The magnitude of such voltage will be determined by the resistor network, and thus mechanism 220 permits a unique identification of the particular characteristics and/or physical size of the probe tip presently attached to the probe. Another form of passive implementation of mechanism 220 would include projecting pins in one of connectors 220 and 210 that push spring-loaded contacts (or the equivalent) in the other of the connectors. Different probe tips would cause different ones of the spring-loaded contacts to be depressed. The contacts can switch reference voltage(s) such that unique identification of the probe tip characteristics and/or size is achieved.

Electrically, mechanism 220 could include persistent solid state memory storing electrical signals uniquely identifying the characteristic and/or size (or indeed other parameter(s)) of the particular probe tip. These preferably digital stored signals would be carried by appropriate pins within connector 200, to connector 210, via appropriate wires 120 to electronics within system 10, to identify the probe tip. Once so identified, electronics within system 10 would vary parameters of the various electronic circuitry, as needed.

For example, a physically large probe tip would output more detection signal (for a given radiation source) than a smaller probe tip. Mechanism 220 could thus be used to decrease overall system gain (including, as necessary gain of amplifier(s) 90) for the larger probe tip, compared to a smaller probe tip. This would permit the various electronics in system 10 to operate in a more idealized dynamic range, as the detection input signals will essentially be normalized. It may also be desired to use the signals (mechanical and/or electrical) from mechanism 220 to electronically adjust shaping time, acquisition time, frequency characteristics, among other parameters of the system 10 electronics, including discriminator electronics 80.

If desired, system 10 recognition of electrical and/or mechanical signals from mechanism 220 can be used to control a signal to visual and/or acoustic output devices (e.g., 32, 32', 34, 34') to confirm to the user the specific probe now being used.

Using the present invention, within seconds a surgeon or other practitioner-user can remove one probe detector tip from the probe and attach another probe detector tip. The time required to remove one tip and attach another is on the order of perhaps five seconds. This flexibility permits readily tailoring the size and/or detection characteristics of the probe to the task immediately at hand. There is no need to provide and maintain a plurality of probes, of various sizes and detection characteristics. Instead, a single probe may be rapidly coupled to any of a variety of different probe detector tips. If desired, probe tips 40 may provide slots permitting insertion of a biopsy needle into the examination site to facilitate a probe-guided biopsy of areas of interest. By way of example, such needles are useful in locating a lymph node that exhibits high gamma activity. In lieu of a biopsy needle, the present invention also permits attaching a scalpel blade or a marker pen tip (used to mark biopsy sample regions) to a probe tip. In a still further embodiment, the probe tip may be combined with a tumor ablation device which can then be guided to the tumor by the probe signal.

Figure 3:
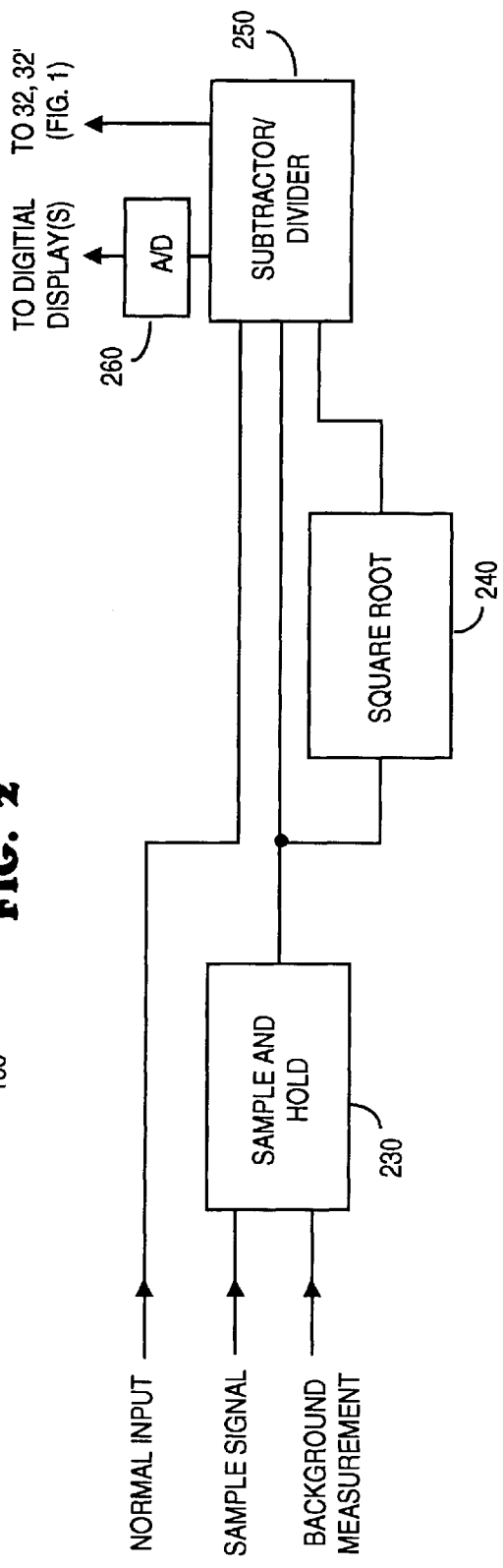
FIG. 3 is a simplified block diagram depicting a system for calculating z-scores in real-time.

FIG. 3 depicts a preferred implementation of circuitry to determine Z-score. A value for n is determined by the surgeon or other user placing the probe tip over an area close to the surgical field in which it is known no structure of interest (e.g., a tumor or lymph node) is located. The present voltage level associated with the background signal is acquired by sample and hold unit 230. To facilitate signal capture, switch 110 on probe 20 may be pressed (or otherwise activated) by the user to generate a "sample signal" control signal. This sample signal is coupled to unit 230 to command sample (or acquisition) of a new signal, or to command retention (hold) of a present signal.

The standard deviation σ for this background value is equivalent to the square root of the number of counts. Thus in FIG. 3, a square root module 240 (e.g., an Analog Device AD538 real-time analog computational circuit) is coupled to receive the output signal stored in sample and hold unit 230.

The user also surveys the surgical field for areas of tracer localization, and Z-scores are continuously calculated by subtracting the sample and held stored voltage level (n) from the present signal reading (s). The (s−n) difference is then divided by the standard deviation of n. In FIG. 3, the substraction and division is carried out by unit 250, (e.g., an Analog Devices AD734 quadrant Multiplier/divider circuit).

The output (Z-score) is thus in analog form and can be used to drive an analog display device, e.g., display 32, 32'. If desired, an analog-to-digital ("A/D") converter 260 could be used to digitize the analog output signal, for example to drive a digital display that may in fact be 32 and/or 32'. Of course the present invention may calculate or permit to be calculated functions other than Z-score.

Figure 4:
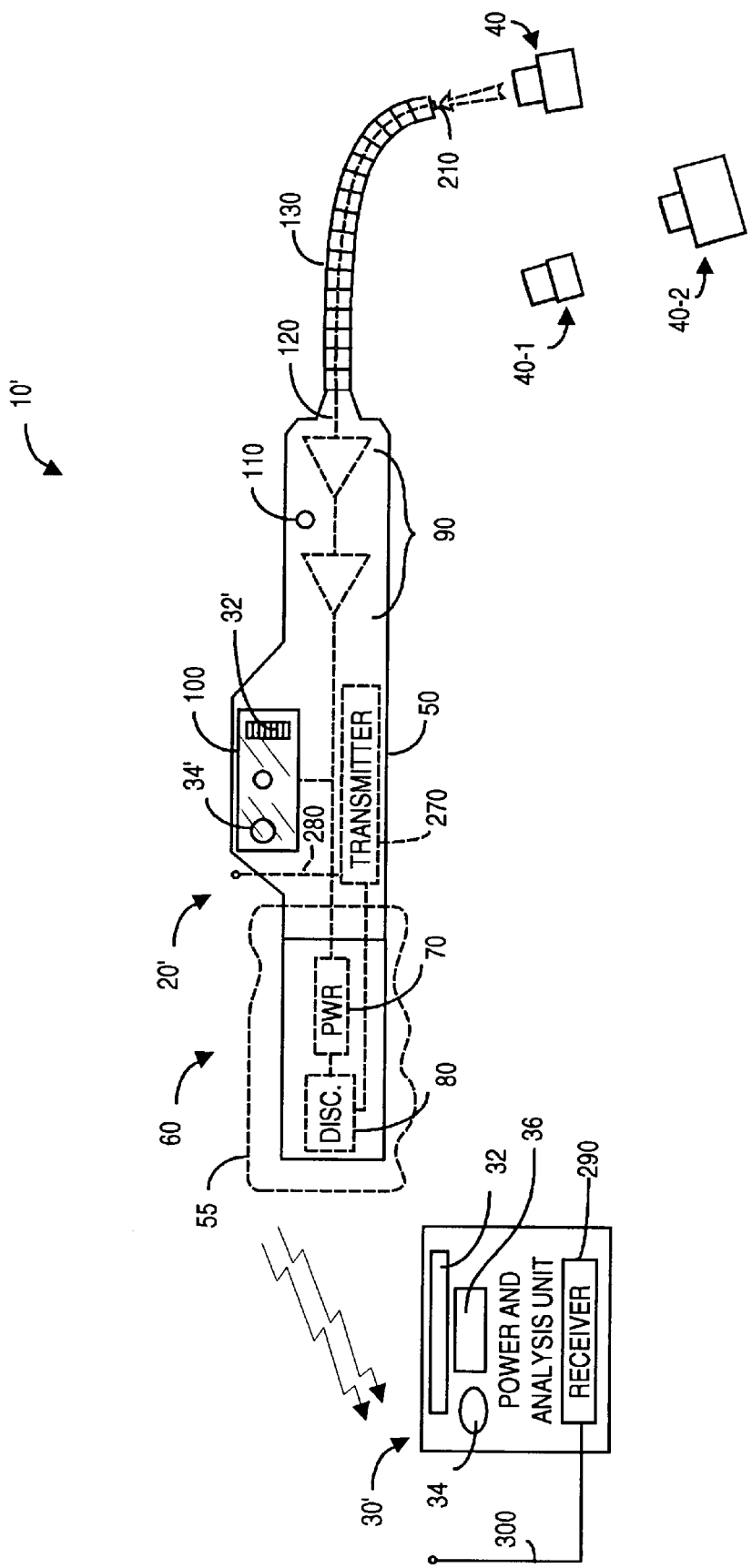
FIG. 4 depicts a wireless embodiment of the present invention.

FIG. 4 depicts a wireless embodiment of the present invention. System 10', probe 20' and power and analysis unit 30' are somewhat similar to what has been described with respect to FIG. 1, except that probe 20' operates wirelessly from unit 30'. Internal to probe 20' is a transmitter 50 that is coupled to receive processed signals from electronics 80 and/or 90, and to transmit these signals via antenna 280. A self-contained battery power supply within probe 20' will power the in-probe electronics and transmitter. It is understood that unit 30' may be implemented with a conventional computer, e.g., a laptop or desktop unit, programmed to electronically signal process data received from the probe.

Typically, within the same room there is provided a power and analysis unit 30' that includes a receiver 290 and receiving antenna 300. Receiver 290 receives the signals transmitted (shown as jagged lines) by antenna 280 in probe 20', for any further signal processing within unit 30'.

Indeed, transmitter 270 and receiver 290 could each be transceivers. Thus, for example, after antenna 300 receives incoming transmitted signals from probe 20', electronics within unit 30' could process these signals and transmit back information to antenna 280 and transmitter 270. Such information might, for example, be the data to be displayed or sounded using devices 32' and/or 34'.

It will be appreciated that while system 10' operates similarly to system 10, system 10' provides greater flexibility to the surgeon or other user-practitioner in that tether 35 is now a wireless communications channel. It is understood that while transmitter or transceiver 270 and receiver or transceiver 290 preferably operate at radio frequencies, they could instead operate at infrared frequency and/or ultrasonic audio frequency. However given that probe 20' may constantly be changing in orientation relative to unit 30', radio frequency transmissions may be preferred.

To recapitulate, the present invention provides a probe system in which probe tips may readily be attached or detached from the distal end of a curved, preferably flexible tube that is affixed to the probe handle or body. The operator or other practitioner-user can thus adjust the orientation of an appropriate detector tip for the task at hand.

The interchangeable detector tips preferably signal their identification to the system to permit automatic compensating changes in the system electronics as a function of the particular probe tip being used. Preferably statistical output capability Z-scores are calculated automatically in real-time using preferably inexpensive electronic devices. Relevant data and information including count rates and statistical output may be displayed directly on the probe body such that the user need not look away from an area of survey to learn such information, or be portrayed by an audio signal of varying frequency or intensity. If desired, the present invention may be implemented as a completely self-contained wireless unit, thus allowing the user more complete freedom from electrical connections to remote system components. User comfort may be promoted by including a customized handle overpiece grip that is removable such that a given probe body may be used by individual users in comfort. Finally, the present invention permits direct radiation probe guided biopsies of suspicious areas.

Modifications and variations may be made to the disclosed embodiments without departing from the subject and spirit of the invention as defined by the following claims.

What is claimed is:

1. A modular radiation detecting probe system comprising:
a probe body having a handle portion and a distal portion; and
an extension member having a first end coupled to said distal portion of said probe body, and having a second end adapted to matingly attach and detach with at least a chosen one of a first probe tip and a second probe tip;
wherein said first probe tip differs from said second probe tip in at least one of (a) probe tip size, and (b) at least one radiation detecting characteristic.

2. The system of claim 1, wherein said probe system further includes an electronic signal acquisition system, disposed within said probe body, coupled to receive a signal output from a said probe tip and to signal process said signal so as to discriminate at least in part between a noise signal and a radiation signal detected by said probe tip.

3. The system of claim 2, wherein said probe system further includes at least one signal device, disposed in said probe body and coupled to said signal acquisition system, to signal at least one characteristic related to a detected said radiation signal.

4. The system of claim 3, wherein:
said signal device has at least one characteristic selected from a group consisting of (a) said device is a visual display device, and (b) said device is a sound generating device; and
said characteristic is selected from a group consisting of (a) magnitude of a detected said radiation signal, (b) relative signal to noise ratio associated with a detected said radiation signal, and (c) Z-score associated with a detected said radiation signal.

5. The system of claim 2, further including a transmitter, housed within said probe body, coupled to an output of said acquisition system, transmitting radiation detected data for reception by an adjacent receiving system;
wherein said transmitter transmits in at least one frequency range selected from a group consisting of (a) radio frequency, (b) infrared frequency, and (c) ultrasonic frequency.

6. The system of claim 2, further including at least one user-selectable control, mounted on said probe body and coupled to said acquisition system, to control acquisition of a probe tip radiation detected signal.

7. The system of claim 1, wherein said extension member is articulated.

8. The system of claim 1, further including:

an external signal processor unit coupled to said probe handle to process a probe tip radiation detected signal;

wherein said signal processor unit is coupled in at least one mode selected from a group consisting of (a) coupling is via at least one electrical wire, (b) coupling is wireless, (c) coupling is via radio frequency transmission, (d) coupling is via infrared transmission, and (e) coupling is via ultrasonic transmission.

9. The system of claim 8, wherein said external signal processor is a computer.

10. A modular radiation detecting probe system comprising:

a probe body having a handle portion and a distal portion;

an extension member having a first end coupled to said distal portion of said probe body, and having a second end adapted to matingly attach and detach with at least a chosen one of a first probe tip and a second probe tip; and at least said first probe tip and said second probe tip;

wherein said first probe tip differs from said second probe tip in at least one of (a) probe tip size, and (b) at least one radiation detecting characteristic; and wherein attachment and detachment of a said probe tip is such that a probe tip may be replaced on said second end of said extension member in less than 30 seconds.

11. The system of claim 10, wherein said probe system further includes an electronic signal acquisition system, disposed within said probe body, coupled to receive a signal output from a said probe tip and to signal process said signal so as to discriminate at least in part between a noise signal and a radiation signal detected by said probe tip.

12. The system of claim 11, wherein said probe system further includes at least one signal device, disposed in said probe body and coupled to said signal acquisition system, to signal at least one characteristic related to a detected said radiation signal.

13. The system of claim 12, wherein said characteristic is selected from a group consisting of (a) magnitude of a detected said radiation signal, (b) relative signal to noise ratio associated with a detected said radiation signal, and (c) Z-score associated with a detected said radiation signal.

14. The system of claim 11, further including a transmitter, housed within said probe body, coupled to an output of said acquisition system, transmitting radiation detected data for reception by an adjacent receiving system;

wherein said transmitter transmits in at least one frequency range selected from a group consisting of (a) radio frequency, (b) infrared frequency, and (c) ultrasonic frequency.

15. The system of claim 11, further including:

an external signal processor unit coupled to said probe handle to process a probe tip radiation detected signal;

wherein said signal processor unit is coupled in at least one mode selected from a group consisting of (a) coupling is via at least one electrical wire, (b) coupling is wireless, (c) coupling is via radio frequency transmission, (d) coupling is via infrared transmission, and (e) coupling is via ultrasonic transmission.

16. A method of changing probe tips in a radiation detecting probe, comprising the following steps:

(a) providing a probe body having a handle portion, a distal portion, and an extension member having a first end coupled to said distal portion of said probe body, and having a second end adapted to matingly attach and detach with at least a chosen one of a first probe tip and a second probe tip; and (b) attaching a said probe tip to said second end;

wherein step (b) may be carried out in less than 30 seconds.

17. The method of claim 16, further including an intermediate step (a-1) comprising removing a said probe tip from said second end prior to carrying out step (b);

wherein step (a-1) and step (b) together may be carried out in less than 30 seconds.

18. The method of claim 16, wherein step (a) includes providing a said probe body that includes an electronic signal acquisition system coupled to receive a signal output from a said probe tip and to signal process said signal so as to discriminate at least in part between a noise signal and a radiation signal detected by said probe tip.

19. The method of claim 18, further including:

providing said second end with means for recognizing at least one signal detection characteristic of an attached said probe tip; and using data obtained by said means for recognizing to normalize at least one parameter within said acquisition system.

20. A modular radiation detecting probe system comprising:

a probe body having a handle portion and a distal portion;

an extension member having a first end coupled to said distal portion of said probe body, and having a second end adapted to matingly attach and detach with at least a chosen one of a first probe tip and a second probe tip;

an electronic signal acquisition system, disposed within said probe body, coupled to receive a signal output from a said probe tip and to signal process said signal so as to discriminate at least in part between a noise signal and a radiation signal detected by said probe tip; and at least one signal device, disposed in said probe body and coupled to said signal acquisition system, to signal at least one characteristic related to a detected said radiation signal, wherein said signal device has at least one characteristic selected from a group consisting of (a) said device is a visual display device, and (b) said device is a sound generating device; and said characteristic is selected from a group consisting of (a) magnitude of a detected said radiation signal, (b) relative signal to noise ratio associated with a detected said radiation signal, and (c) Z-score associated with a detected said radiation signal.

21. A modular radiation detecting probe system comprising:

a probe body having a handle portion and a distal portion;

an extension member having a first end coupled to said distal portion of said probe body, and having a second end adapted to matingly attach and detach with at least a chosen one of a first probe tip and a second probe tip;

an external signal processor unit coupled to said probe handle to process a probe tip radiation detected signal, wherein said external signal processor unit is a computer coupled in at least one mode selected from a group consisting of (a) coupling is via at least one electrical wire, (b) coupling is wireless, (c) coupling is via radio frequency transmission, (d) coupling is via infrared transmission, and (e) coupling is via ultrasonic transmission.

* * * * *